US010449009B2

(12) United States Patent
Hatakeyama et al.

(10) Patent No.: US 10,449,009 B2
(45) Date of Patent: Oct. 22, 2019

(54) MEDICAL SYSTEM (71) Applicant: OLYMPUS CORPORATION, Tokyo (JP)

(72) Inventors: Naoya Hatakeyama, Tokyo (JP); Masatoshi Iida, Tokyo (JP); Hiroshi Wakai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 487 days.

(21) Appl. No.: 15/235,396

(22) Filed: Aug. 12, 2016

(65) Prior Publication Data

US 2016/0346054 A1 Dec. 1, 2016

Related U.S. Application Data

(63) Continuation of application No. PCT/JP2015/052641, filed on Jan. 30, 2015.

(30) Foreign Application Priority Data

Feb. 27, 2014 (JP) .................................. 2014-036297

(51) Int. Cl.
*A61B 34/37* (2016.01)
*A61B 34/30* (2016.01)
(Continued)

(52) U.S. Cl.
CPC ........ *A61B 34/37* (2016.02); *A61B 17/00234* (2013.01); *A61B 34/30* (2016.02);
(Continued)

(58) Field of Classification Search
CPC .... A61B 17/00234; A61B 2017/00296; A61B 2017/00725; A61B 34/30; A61B 34/37;
(Continued)

(56) References Cited

U.S. PATENT DOCUMENTS 7,060,027 B2 * 6/2006 Maeda ............... A61B 1/00039
600/117
7,728,280 B2 * 6/2010 Feilkas .................. A61B 34/20
250/208.1
(Continued)

FOREIGN PATENT DOCUMENTS

EP 2335553 A1 6/2011
EP 2 881 061 A1 6/2015
(Continued)

OTHER PUBLICATIONS

International Search Report dated Mar. 31, 2015 issued in PCT/JP2015/052641.
(Continued)

*Primary Examiner* — Amanda K Hulbert
*Assistant Examiner* — Philip C Edwards
(74) *Attorney, Agent, or Firm* — Scully, Scott, Murphy & Presser, P.C.

(57) ABSTRACT

A medical system includes: a treatment tool including a treatment portion configured to treat a living body, a joint portion configured to move the treatment portion, a first indicator portion provided to correspond to a position of the joint portion, a sheath portion connected to the joint portion, and a driving portion connected to the sheath portion and configured to displace the joint portion; an overtube including a flexible tube portion having a distal end and a proximal end and holding the treatment tool such that the treatment portion is capable of protruding from the distal end, and a second indicator portion provided at the flexible tube portion to identify a predefined space where calibration of the treatment tool is performed; and a calibration mechanism configured to calibrate the treatment tool when the first and second indicator portions have a predetermined positional relationship.

8 Claims, 11 Drawing Sheets

(51) Int. Cl.
*A61B 90/00* (2016.01)
*A61B 17/00* (2006.01)

(52) U.S. Cl.
CPC .... *A61B 90/08* (2016.02); *A61B 2017/00296* (2013.01); *A61B 2017/00725* (2013.01); *A61B 2034/301* (2016.02); *A61B 2090/0811* (2016.02)

(58) Field of Classification Search
CPC ............ A61B 2034/301; A61B 90/08; A61B 2090/0811
USPC .............................................................. 606/1
See application file for complete search history.

(56) References Cited

U.S. PATENT DOCUMENTS

| | | | |
|---|---|---|---|
| 8,183,520 B2 * | 5/2012 | Prisco | G01B 11/18 250/227.14 |
| 2003/0045778 A1 * | 3/2003 | Ohline | A61B 1/0053 600/114 |
| 2008/0103491 A1 | 5/2008 | Omori et al. | |
| 2008/0114494 A1 | 5/2008 | Nixon | |
| 2009/0012365 A1 | 1/2009 | Ueno et al. | |
| 2009/0112060 A1 | 4/2009 | Sugiyama et al. | |
| 2009/0292166 A1 | 11/2009 | Ito et al. | |
| 2010/0082041 A1 | 4/2010 | Prisco | |

FOREIGN PATENT DOCUMENTS

| | | |
|---|---|---|
| EP | 3 109 013 A1 | 12/2016 |
| JP | H10-174686 A | 6/1998 |
| JP | 2001-145638 A | 5/2001 |
| JP | 2007-029167 A1 | 2/2007 |
| JP | 2008-104854 A | 5/2008 |
| JP | 2009-101077 A | 5/2009 |
| JP | 2009-279250 A | 12/2009 |
| JP | 2012-504016 A | 2/2012 |
| WO | WO 2010/140441 A1 | 12/2010 |
| WO | 2014/021122 A1 | 2/2014 |

OTHER PUBLICATIONS

Extended Supplementary European Search Report dated Oct. 6, 2017 received in 15755299.3.

* cited by examiner

MEDICAL SYSTEM

This application is a continuation application based on PCT Patent Application No. PCT/JP2015/052641, filed Jan. 30, 2015, whose priority is claimed on Japanese Patent Application No. 2014-036297, filed in Feb. 27, 2014. The contents of both the PCT Patent Application and the Japanese Patent Application are incorporated herein by reference.

BACKGROUND OF THE INVENTION

Field of the Invention

Embodiments of the present invention relate to a medical system.

Description of Related Art

A medical system configured to drive a treatment tool of a manipulator by virtue of rotational power of a motor using a wire is known (for example, refer to United States Patent Application, Publication No. 2008-0114494). In such a medical system, calibration is performed by moving one of a pair of grip parts of the manipulator toward the other grip part and measuring a displacement position and a torque of the grip part at that time.

SUMMARY OF THE INVENTION

According to a first aspect of the present invention, a medical system comprising: a treatment tool including a treatment portion configured to treat a living body, a joint portion configured to move the treatment portion, a first indicator portion provided to correspond to a position of the joint portion, a sheath portion connected to the joint portion, and a driving portion connected to the sheath portion and configured to displace the joint portion; an overtube including a flexible tube portion having a distal end and a proximal end, the flexible tube portion holding the treatment tool such that the treatment portion is capable of protruding from the distal end, and a second indicator portion provided at the flexible tube portion to identify a predefined space in which calibration of the treatment tool is performed; and a calibration mechanism configured to calibrate the treatment tool when the first indicator portion and the second indicator portion have a predetermined positional relationship.

According to a second aspect of the present invention, in the medical system according to the first aspect, the first indicator portion may include a detecting means for determining that the first indicator portion and the second indicator portion have the predetermined positional relationship when the second indicator portion is positioned closer than a predetermined distance.

According to a third aspect of the present invention, in the medical system according to the first aspect, the second indicator portion may include a detecting means for determining that the first indicator portion and the second indicator portion have the predetermined positional relationship when the first indicator portion is positioned closer than a predetermined distance.

According to a fourth aspect of the present invention, in the medical system according to any one of the first to third aspects, the overtube may include a channel into which the treatment portion, the joint portion, the first indicator portion, and the sheath portion are capable of being inserted. The space may be defined inside the channel.

According to a fifth aspect of the present invention, in the medical system according to any one of the first to fourth aspects, the second indicator portion may include an imaging unit configured to image the first indicator portion.

According to a sixth aspect of the present invention, in the medical system according to any one of the first to fifth aspects, the calibration mechanism may be allowed to start calibration only when the first indicator portion and the second indicator portion have the predetermined positional relationship.

According to a seventh aspect of the present invention, in the medical system according to the first aspect, the first indicator portion and the second indicator portion may include a projecting and recessed structure in which the first indicator portion and the second indicator portion are mated to each other when the first indicator portion and the second indicator portion have the predetermined positional relationship.

According to an eighth aspect of the present invention, in the medical system according to any one of the first to seventh aspects, the calibration mechanism may include: a determination unit configured to detect a positional relationship between the first indicator portion and the second indicator portion and determine whether or not the first indicator portion and the second indicator portion have the predetermined positional relationship; and an automatic start unit configured to start calibration when a state changes from a state in which the determination unit determines that the first indicator portion and the second indicator portion do not have the predetermined positional relationship to a state in which the determination unit determines that the first indicator portion and the second indicator portion have the predetermined positional relationship.

According to a ninth aspect of the present invention, in the medical system according to any one of the first to seventh aspects, the calibration mechanism may include: a determination unit configured to detect a positional relationship between the first indicator portion and the second indicator portion and determine whether or not the first indicator portion and the second indicator portion have the predetermined positional relationship; and an automatic stop unit configured to interrupt or terminate calibration when the calibration is being executed and a state changes from a state in which the determination unit determines that the first indicator portion and the second indicator portion have the predetermined positional relationship to a state in which the determination unit determines that the first indicator portion and the second indicator portion do not have the predetermined positional relationship.

DETAILED DESCRIPTION OF THE INVENTION

A medical system and a control method according to embodiments of the invention will now be described with reference to the accompanying drawings. Note that, in the following drawings, the scale of each member is appropriately adjusted in order to make them recognizable.

(First Embodiment)

Figure 1:
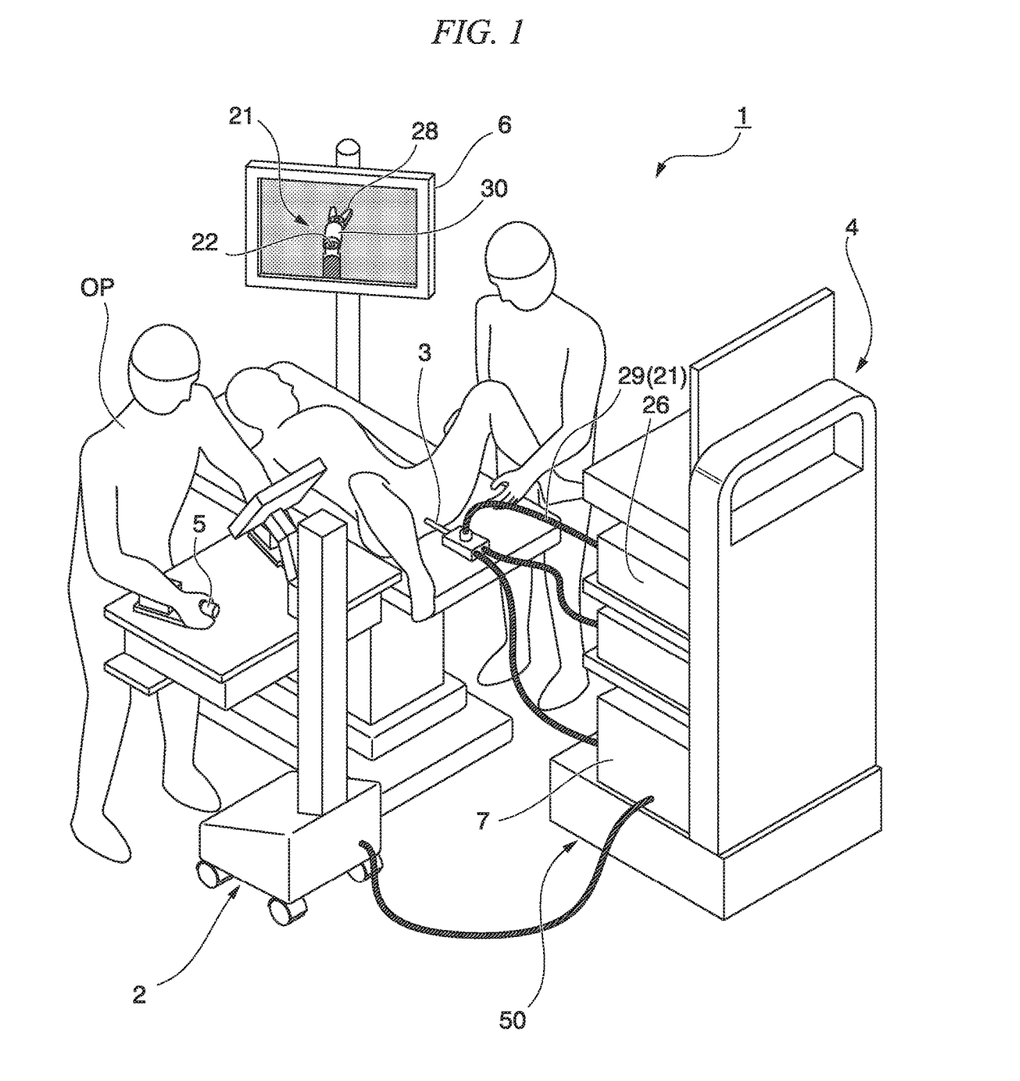
FIG. 1 is a perspective view schematically illustrating an entire configuration of a medical system according to a first embodiment.

FIG. 1 is a perspective view schematically illustrating an entire configuration of a medical system according to a first embodiment. The medical system according to this embodiment is a master-slave type system. Specifically, as illustrated in FIG. 1, a medical system 1 has a master manipulator 2 configured to allow an operator OP to perform a treatment manipulation, a main body 4 provided with an endoscope 3, and a control unit 50 configured to control an operation of the endoscope 3 and a treatment tool 21 from the main body 4 in response to a manipulation of the master manipulator 2 (refer to FIG. 3).

The master manipulator 2 has a master arm 5 operated by the operator OP, a display device 6 for displaying image information such as images captured by the endoscope 3, and a controller 7 configured to generate a manipulation instruction for operating the main body 4 based on the operation of the master arm 5.

The master arm 5 is a manipulation portion provided to operate the endoscope 3 and the treatment tool 21. Although not illustrated in detail in the drawings, the master manipulator 2 is provided with two master arms 5 to correspond to left and right hands of the operator OP.

Figure 2:
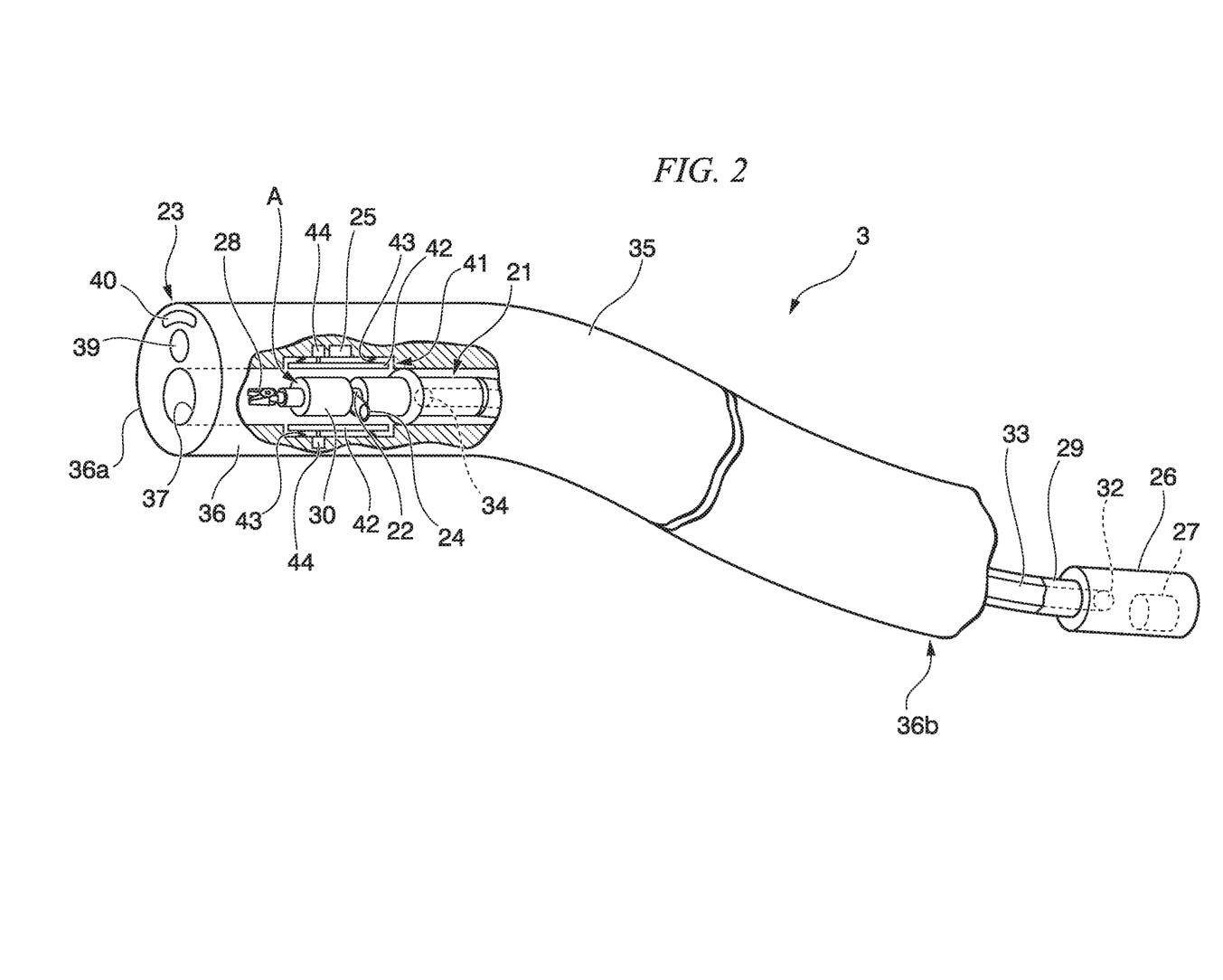
FIG. 2 is a partially cutaway perspective view illustrating an endoscope in the medical system according to the first embodiment.

The display device 6 is a device for displaying an image of a treatment target region captured by an observation device 23 installed in the endoscope 3 (refer to FIG. 2). On the display device 6, a treatment portion 28 or a joint portion 22 of the treatment tool 21, which will be described below, is also displayed along with the treatment target region.

The controller 7 generates a manipulation instruction for operating the main body 4 based on the operation of the master arm 5.

The main body 4 is connected to the endoscope 3 and the treatment tool 21 to control operations of each of the endoscope 3 and the treatment tool 21.

Next, a configuration of the treatment tool 21 that can be attached to the endoscope 3 will be described. FIG. 2 is a partially cutaway perspective view illustrating the endoscope 3 in the medical system according to the first embodiment. As illustrated in FIG. 2, the treatment tool 21 that can be attached to the endoscope 3 has the treatment portion 28, the joint portion 22, an arm portion 30, a first indicator portion 24, a sheath portion 29, and a treatment tool driving portion 26.

The treatment portion 28 is provided to treat a living body. The treatment portion 28 is, for example, forceps or a scalpel. The treatment portion 28 is driven by the treatment tool driving portion 26 using a wire (not shown) or the like. The joint portion 22 and the arm portion 30 are provided to move the treatment portion 28, and are driven by the treatment tool driving portion 26.

The first indicator portion 24 is arranged in the joint portion 22. The first indicator portion 24 according to this embodiment is a detection target, a position of which can be detected by a second indicator portion 25 (which will be described below) provided in the endoscope 3. A configuration of the first indicator portion 24 is determined depending on a configuration of the second indicator portion 25. In this embodiment, the first indicator portion 24 is a magnet.

The sheath portion 29 is formed in a flexible tubular shape. The joint portion 22 is arranged in a distal side of the sheath portion 29, and the treatment tool driving portion 26 is arranged in a proximal side of the sheath portion 29. A wire 33 for moving the joint portion 22 and the arm portion 30 is arranged inside the sheath portion 29.

The treatment tool driving portion 26 is connected to the proximal side of the sheath portion 29. The treatment tool driving portion 26 has a motor 27, an encoder 31, a driving side rotation body 32, a driven side rotation body 34, and the wire 33. The motor 27 is provided one by one, for example, depending on degrees of freedom of the joint portion 22 and the treatment portion 28. It should be noted that the motor 27 may be a step motor, and in this case, the encoder 31 may not be provided. The encoder 31 is attached to an output shaft of the motor 27 in, for example, a non-contact manner. The encoder 31 is electrically connected to the control unit 50. The driving side rotation body 32 is connected to the output shaft of the motor 27 by interposing a deceleration mechanism (not shown) therebetween. The driving side rotation body 32 is, for example, a pulley. The driven side rotation body 34 is arranged in the vicinity of the distal end of the sheath portion 29, and is connected to the joint portion 22. As the driven side rotation body 34 rotates, the joint portion 22 operates. The driven side rotation body 34 is, for example, a pulley. The wire 33 is an annular wire having one end looped over the driving side rotation body 32 and the other end looped over the driven side rotation body 34. The wire 33 is movably housed in the sheath portion 29. It should be noted that the wire 33 may be partially connected to the driving side rotation body 32 or the driven side rotation body 34 in order to prevent slippage with respect to the driving side rotation body 32 or the driven side rotation body 34.

Next, a configuration of the endoscope 3 will be described. The endoscope 3 has an overtube 35 and the observation device 23. The overtube 35 is a flexible long member inserted into a body of a patient. The overtube 35 includes a flexible tube portion 36 having a treatment tool channel 37, the second indicator portion 25, and a calibration sensor 41 for calibrating the treatment tool 21. In addition, in this embodiment, a distal portion of the overtube 35 can be curved by receiving the control of the control unit 50.

The flexible tube portion 36 has a distal end 36a and a proximal end 36b, and holds the treatment tool 21 such that the treatment portion 28 of the treatment tool 21 inserted into the treatment tool channel 37 can protrude from the distal end 36a.

The treatment tool channel 37 is a tubular portion having one end opened to the distal end 36a of the flexible tube portion 36 and the other end opened to the proximal end 36b of the flexible tube portion 36. Part of the treatment tool 21 inserted into a living body, such as the treatment portion 28, the joint portion 22, the first indicator portion 24, and the sheath portion 29, can be inserted into the treatment tool channel 37.

The second indicator portion 25 is positioned inside the flexible tube portion 36 to correspond to a position of a space A predefined as a space for calibrating the treatment tool 21. In this embodiment, the space A for calibrating the treatment tool 21 is an internal space of the distal portion of the treatment tool channel 37, and is set in an area where the calibration sensor 41 is arranged. The second indicator portion 25 of this embodiment is a detecting means that detects the approach of the first indicator portion 24 within a predetermined distance. In this embodiment, the first indicator portion 24 provided in the treatment tool 21 is a magnet, and the second indicator portion 25 provided in the flexible tube portion 36 has a Hall element that detects the magnet.

The calibration sensor 41 is a sensor for detecting a load applied to the joint portion 22 at the time of calibration of an operation of the joint portion 22 in the treatment tool 21. In this embodiment, the calibration sensor 41 includes a movable body 42 pressed by the joint portion 22, an elastic member 43 that connects the movable body 42 and the treatment tool channel 37, and a movement amount sensor 44 that measures a movement amount of the movable body 42.

The observation device 23 is a device for observing a treatment target region using an imaging portion 39 and a lighting portion 40. The observation device 23 has the imaging portion 39 and the lighting portion 40. The imaging portion 39 has, for example, an area image sensor capable of capturing images of the treatment target region and the treatment portion 28. The lighting portion 40 can radiate illuminating light toward the treatment target region.

Figure 3:
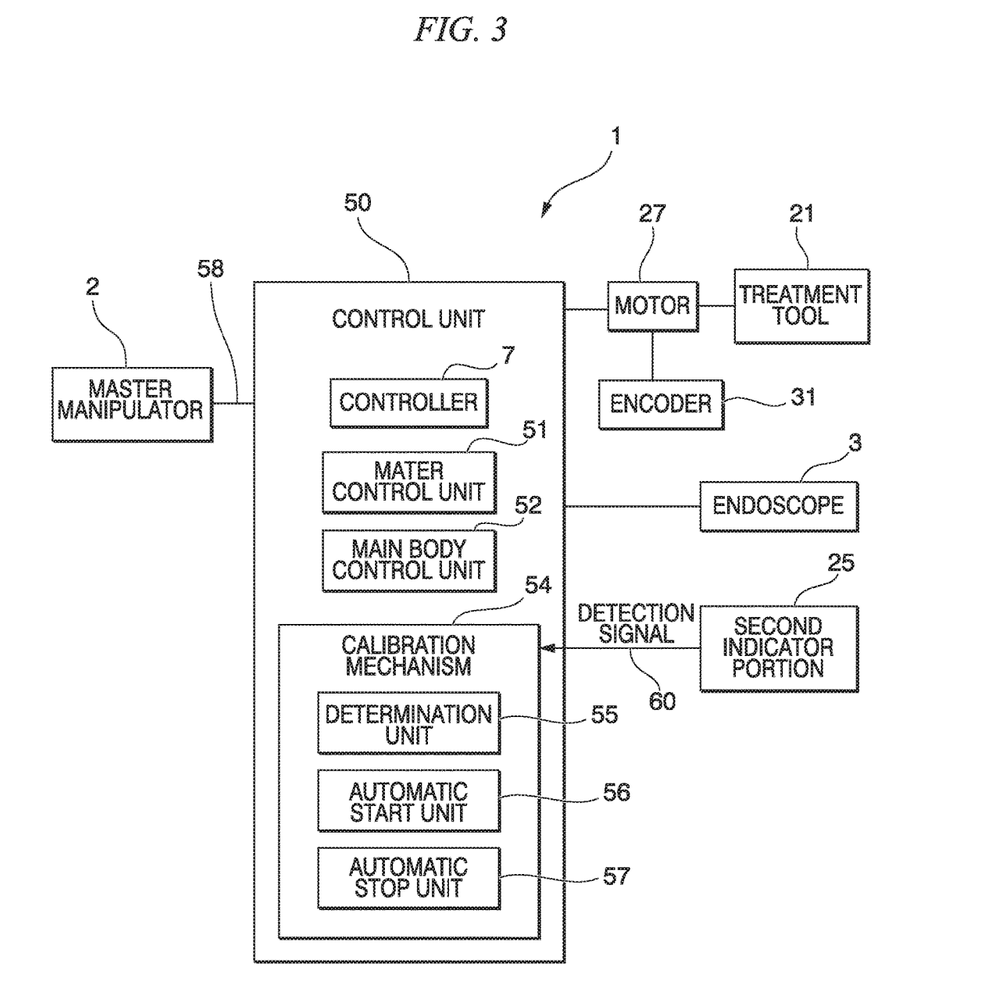
FIG. 3 is a block diagram illustrating an exemplary medical system according to the first embodiment.

FIG. 3 is a block diagram illustrating an exemplary medical system according to the first embodiment. As illustrated in FIG. 3, the control unit 50 of the medical system 1 has a master control unit 51, a main body control unit 52, a calibration mechanism 54, and the controller 7.

The master control unit 51 receives a manipulation input (an input) 58 of the master manipulator 2 and processes the input. The main body control unit 52 outputs a drive signal for the endoscope 3 and the treatment tool 21 based on an instruction from the master control unit 51.

The calibration mechanism 54 calibrates the treatment tool 21 when the first and second indicator portions 24 and 25 (refer to FIG. 2) have a predetermined positional relationship. The calibration mechanism 54 has a determination unit 55, an automatic start unit 56, and an automatic stop unit 57.

The determination unit 55 detects a positional relationship between the first indicator portion 24 and the second indicator portion 25, and determines whether the first and second indicator portions 24 and 25 have the predetermined positional relationship. In this embodiment, the predetermined positional relationship is set depending on a positional relationship of the joint portion 22 of the treatment tool 21 in the space A where the calibration sensor 41 is arranged. Specifically, when the determination unit 55 detects that the first indicator portion 24 exists within a detectable area of the second indicator portion 25, the determination unit 55 determines that the first indicator portion 24 has the predetermined positional relationship with the second indicator portion 25. In other words, the determination unit 55 determines that the first indicator portion 24 has the predetermined positional relationship with the second indicator portion 25 when the first indicator portion 24 is positioned close to the second indicator portion 25 within a detection limit distance (the predetermined distance in this embodiment) of the second indicator portion 25. The fact that the first indicator portion 24 has the predetermined positional relationship with the second indicator portion 25 means that the joint portion 22 of the treatment tool 21 is positioned in the space A where the calibration sensor 41 is arranged.

The automatic start unit 56 causes the treatment tool 21 to start a predetermined calibration operation when a state changes from a state in which the determination unit 55 determines that the first and second indicator portions 24 and 25 do not have the predetermined positional relationship to a state in which the determination unit 55 determines that the first and second indicator portions 24 and 25 have the predetermined positional relationship.

The automatic stop unit 57 causes the treatment tool 21 to interrupt or terminate the calibration when calibration is being executed and a state changes from the state in which the determination unit 55 determines that the first and second indicator portions 24 and 25 have the predetermined positional relationship to the state in which the determination unit 55 determines that the first and second indicator portions 24 and 25 do not have the predetermined positional relationship. That is, in this embodiment, the calibration is interrupted or forcibly terminated when the joint portion 22 exits from the space A before normal termination of the calibration started by the automatic start unit 56. It should be noted that the automatic stop unit 57 may output a predetermined signal to display a fact that the calibration is not normally terminated on, for example, the display device 6.

Figure 4:
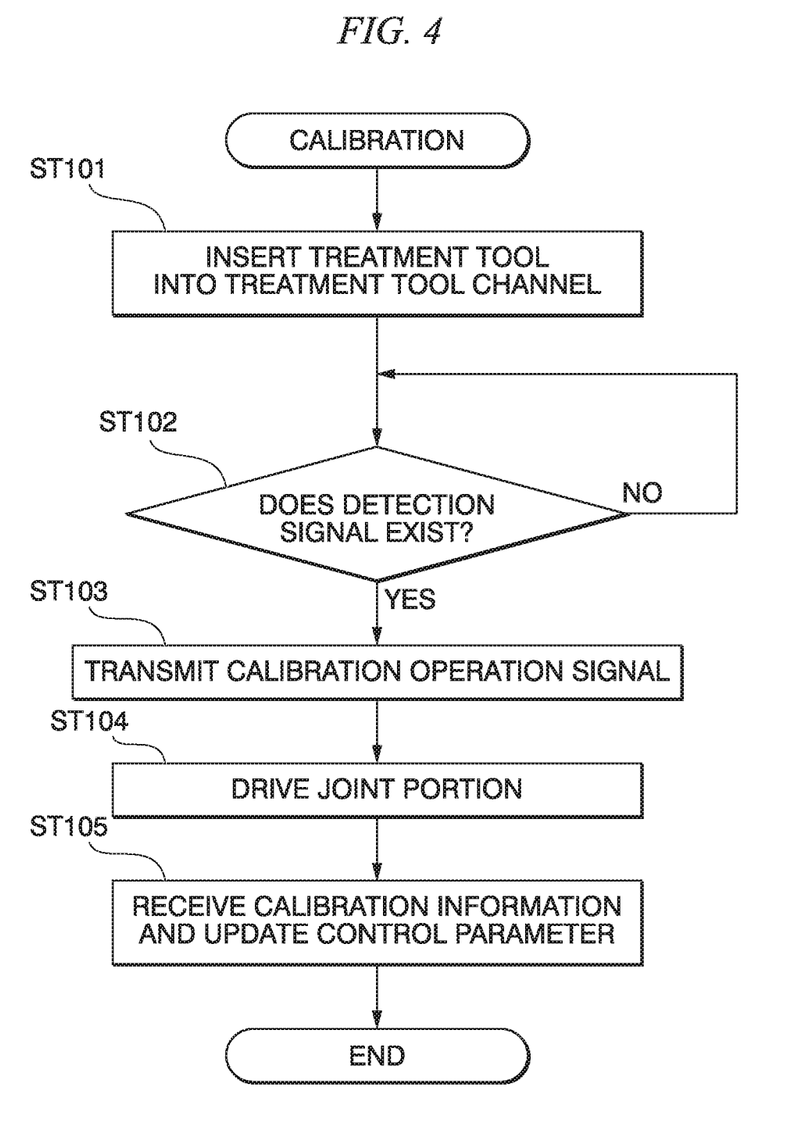
FIG. 4 is a flowchart illustrating a calibration start sequence in the medical system according to the first embodiment.

Next, a flow of the calibration of the treatment tool 21 in the medical system 1 according to this embodiment will be described. FIG. 4 is a flowchart illustrating a calibration start sequence in the medical system according to the first embodiment. As illustrated in FIG. 4, in the calibration start sequence, first, the treatment tool 21 is inserted into the treatment tool channel 37 from an treatment tool insertion hole of the overtube 35 (INSERT TREATMENT TOOL INTO TREATMENT TOOL CHANNEL) (step ST101).

Then, the determination unit 55 determines whether there is a detection signal 60 from the second indicator portion 25 (DOES DETECTION SIGNAL EXIST?) (step ST102). In step ST102, as the treatment tool 21 is inserted into the treatment tool channel 37, the first indicator portion 24 of the treatment tool 21 approaches the second indicator portion 25 of the overtube 35. When the first indicator portion 24 of the treatment tool 21 enters into the detectable area of the second indicator portion 25, the second indicator portion 25 detects the existence of the first indicator portion 24 and generates the detection signal 60. The detection signal 60 generated from the second indicator portion 25 is received by the calibration mechanism 54. The step ST102 is repeated until the detection signal 60 is detected.

The calibration mechanism 54 that has received the detection signal 60 generates a calibration operation signal in reaction to receiving the detection signal 60 (TRANSMIT CALIBRATION OPERATION SIGNAL) (step ST103). That is, in step ST103, the automatic start unit 56 starts calibration when a state changes from the state in which the determination unit 55 determines that the first and second indicator portions 24 and 25 do not have the predetermined positional relationship to the state in which the determination unit 55 determines that the first and second indicator portions 24 and 25 have the predetermined positional relationship.

In response to generation of the calibration operation signal, the motor 27 of the treatment tool driving portion 26 is operated to drive the joint portion 22 of the treatment tool 21 (DRIVE JOINT PORTION) (step ST104). In this case, since the joint portion 22 is arranged at a position of the calibration sensor 41 in the space A of the treatment tool channel 37, the joint portion 22 that is operated to be bent presses the movable body 42 of the calibration sensor 41. The movable body 42 moves as it is pressed by the joint portion 22. The movement of the movable body 42 is measured by the movement amount sensor 44. Using the calibration sensor 41, it is possible to detect the orientation of the joint portion 22 in the space A of the treatment tool channel 37. In addition, it is possible to generate calibration information including a control parameter for defining a relationship between a drive state of the motor 27 and an operational state of the joint portion 22 in the treatment tool driving portion 26. The main body control unit 52 receives the control parameter generated by the calibration sensor 41, and updates the control parameter for operating the treatment tool 21 (RECEIVE CALIBRATION INFORMATION AND UPDATE CONTROL PARAMETER) (step ST105).

Figure 5:
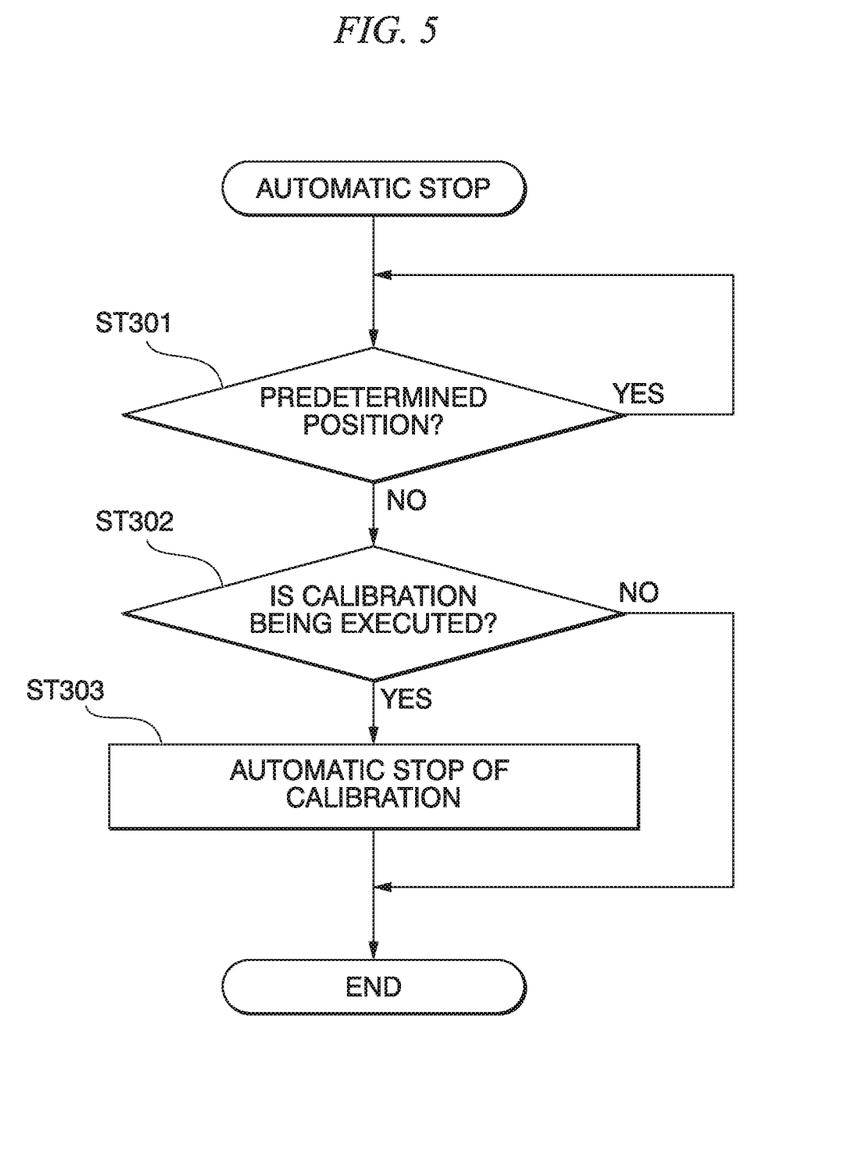
FIG. 5 is a flowchart illustrating an automatic stop operation in calibration of the medical system according to the first embodiment.

FIG. 5 is a flowchart illustrating an automatic stop operation of the calibration in the medical system according to the first embodiment. The medical system 1 according to this embodiment has a means that interrupts or stops calibration after the calibration starts. The automatic stop unit 57 illustrated in FIG. 3 repeatedly determines whether or not the first and second indicator portions 24 and 25 have the predetermined positional relationship by repeatedly detecting whether or not the second indicator portion 25 generates the detection signal 60 (PREDETERMINED POSITIONAL RELATIONSHIP?) (step ST301) (refer to FIG. 5).

When the second indicator portion 25 generates the detection signal 60, the joint portion 22 of the treatment tool 21 is positioned in the space A in which the calibration can be performed. Therefore, the calibration continues. When the second indicator portion 25 does not generate the detection signal 60, the joint portion 22 of the treatment tool 21 has moved from the space A in which the calibration can be performed. Therefore, the automatic stop unit 57 generates a signal for interrupting or stopping the calibration.

In this embodiment, first, it is checked whether the calibration is being executed (IS CALIBRATION BEING EXECUTED?) (step ST302). If the calibration is being executed, the calibration stops (AUTOMATIC STOP OF CALIBRATION) (step ST303). Furthermore, the automatic stop operation of the calibration is terminated when the calibration is normally terminated at a timing at which the second indicator portion 25 does not generate the detection signal 60.

The signal for interrupting or stopping calibration stops an operation of the motor 27 in the treatment tool driving portion 26.

It should be noted that the automatic stop unit 57 may resume the calibration when the second indicator portion 25 re-transmits the detection signal 60 within a predefined time duration after the second indicator portion 25 does not generate the detection signal 60. In this case, the calibration may be resumed in the middle of the calibration process or by executing the entire calibration process again.

According to the first embodiment described above, the calibration is performed after it is detected that the joint portion 22 of the treatment tool 21 is arranged in the space A inside the flexible tube portion 36. Therefore, it is possible to reliably and effectively set a calibration position. In addition, by using the first and second indicator portions 24 and 25, it is possible to easily determine that the joint portion 22 is arranged at a position where the calibration can be suitably performed even when it is difficult to visually recognize the joint portion 22 using the observation device 23 or another device.

Since the calibration automatically starts after the second indicator portion 25 detects the first indicator portion 24, it is possible to simplify manipulation for calibration.

If calibration is being executed when a state changes from a state in which the first indicator portion 24 is detected by the second indicator portion 25 to a state in which the first indicator portion 24 is not detected, the automatic stop unit 57 interrupts or stops the calibration. Therefore, it is possible to prevent the calibration from being performed in an inappropriate positional relationship when the position of the treatment tool 21 is unintentionally changed.

(Modified Example)

It should be noted that, although the example that the first indicator portion 24 is a magnet and the second indicator portion 25 has a Hall element has been described in the embodiment, the first indicator portion 24 may have a Hall element and the second indicator portion 25 may be a magnet.

(Second Embodiment)

Figure 6:
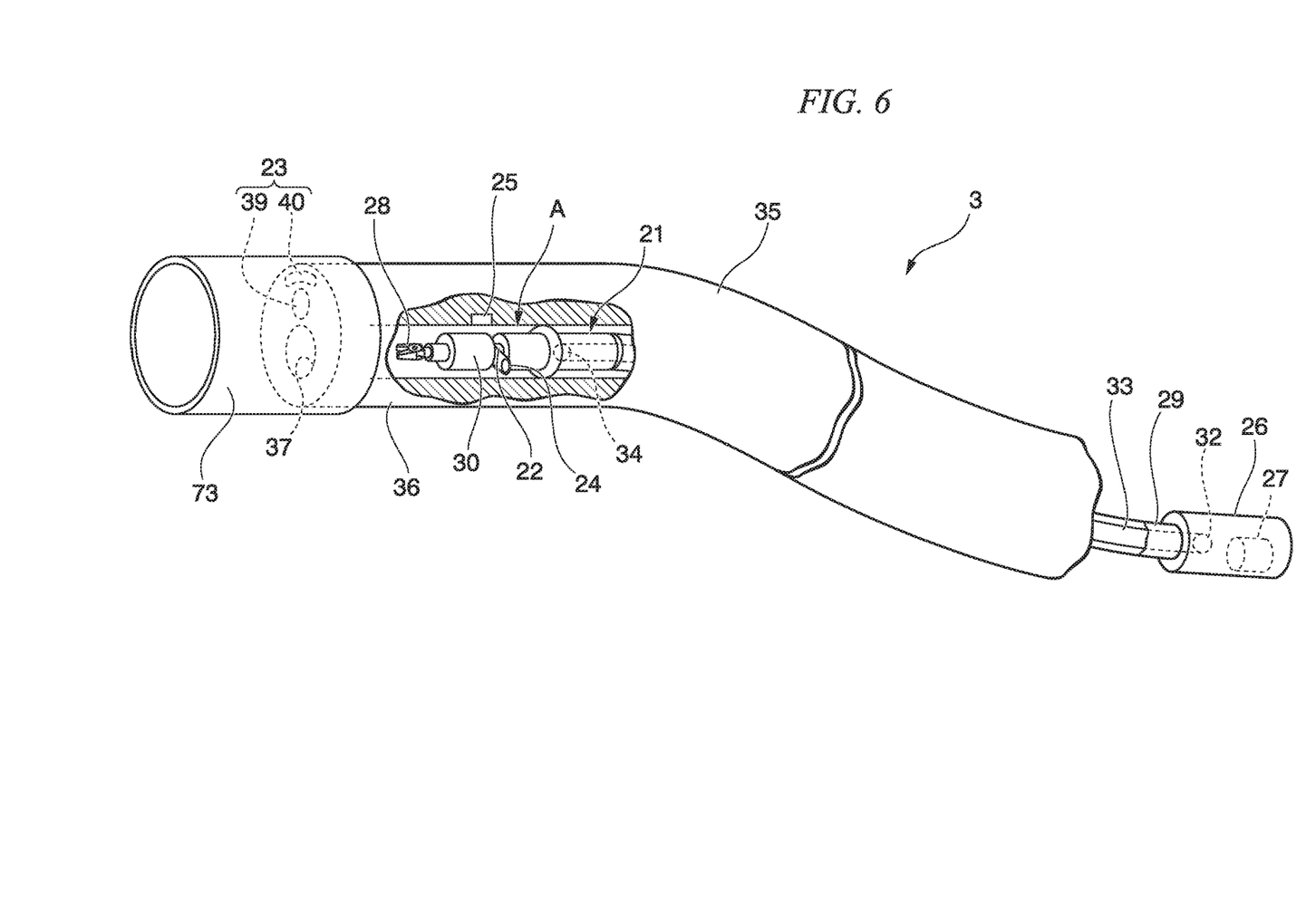
FIG. 6 is a partially cutaway perspective view illustrating an endoscope in a medical system according to a second embodiment.

FIG. 6 is a partially cutaway perspective view illustrating an endoscope in a medical system according to a second embodiment. As illustrated in FIG. 6, in the second embodiment, a space A predefined as a calibration space is set inside a cap 73 mounted on the distal side of the overtube 35 to cover the joint portion 22 of the treatment tool 21. In this embodiment, the cap 73 may be provided with the calibration sensor 41, or calibration may be executed by detecting a tensile force applied to the wire 33 in the treatment tool driving portion 26. For example, in the configuration illustrated in FIG. 6, calibration can be performed by detecting a tensile force applied to the wire 33 in the treatment tool driving portion 26. Specifically, the treatment tool driving portion 26 displaces the joint portion 22 so that the treatment portion 28 comes in contact with an inner circumferential surface of the cap 73. Further, the inner circumferential surface of the cap 73 is pressed by the treatment portion 28 to detect a variation of the tensile force applied to the wire 33.

Even in such a configuration, it is possible to calibrate the treatment tool 21 similar to the first embodiment.

(Third Embodiment)

Figure 7:
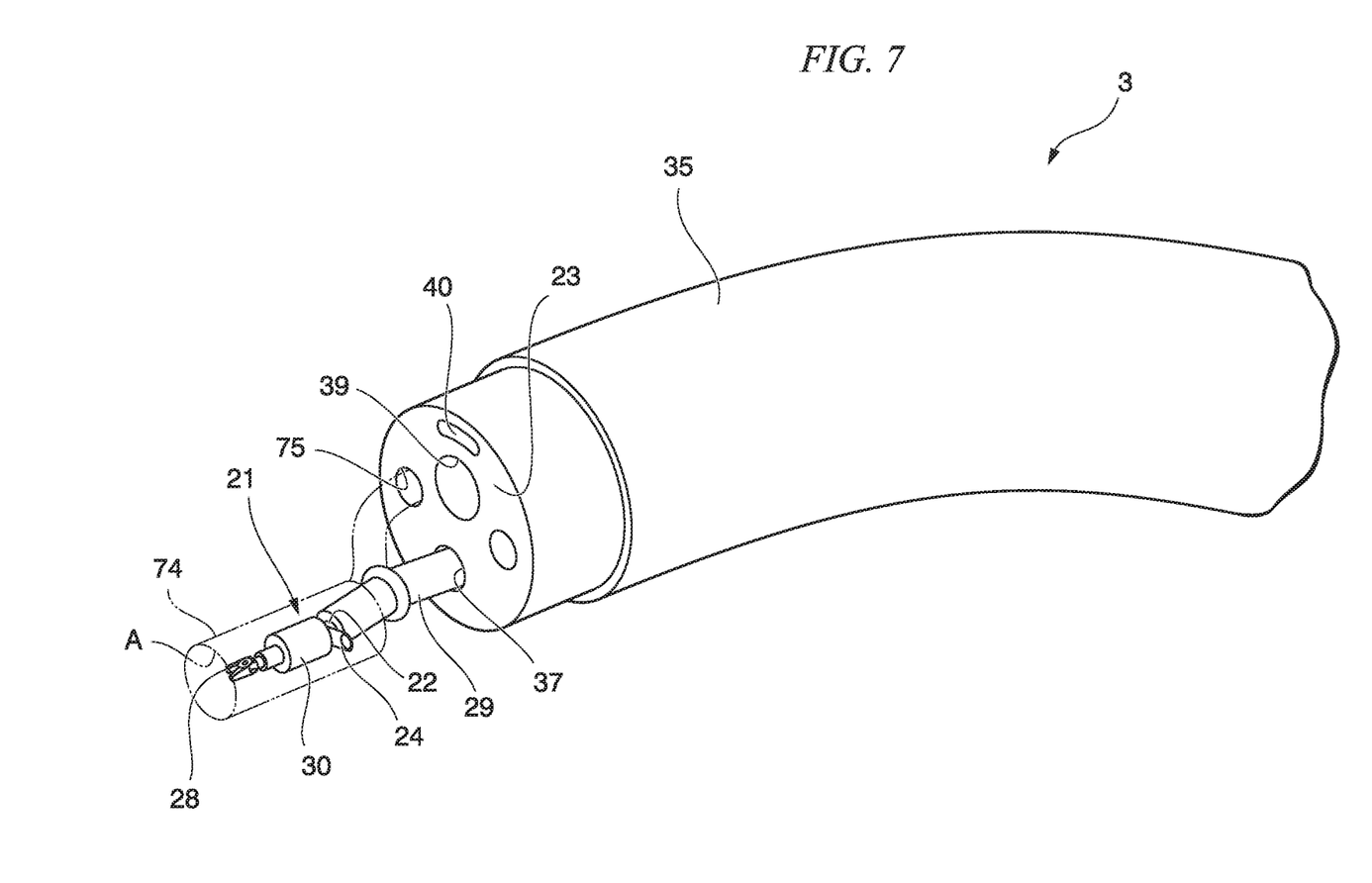
FIG. 7 is a perspective view illustrating an endoscope in a medical system according to a third embodiment.

Next, a third embodiment of the invention will be described. FIG. 7 is a perspective view illustrating an endoscope in a medical system according to the third embodiment. As illustrated in FIG. 7, in the third embodiment, a space A predefined as a calibration space is set by a jig 74 to cover the joint portion 22 of the treatment tool 21. The jig 74 is guided to the distal end of the overtube 35 through another treatment tool channel (a jig channel 75) provided in the overtube 35. The jig 74 has a tubular shape into which the treatment portion 28 and the joint portion 22 of the treatment tool 21 can be inserted. The calibration sensor 41 described in the first embodiment is arranged inside the jig 74. In addition, in this embodiment, the second indicator portion 25 described in the first embodiment is attached to the jig 74. In this embodiment, the second indicator portion 25 is configured to detect the first indicator portion 24 when the treatment tool 21 is properly inserted into the jig 74. As a result, in this embodiment, it is possible to calibrate the treatment tool 21 similar to the first embodiment.

(Fourth Embodiment)

Figure 8:
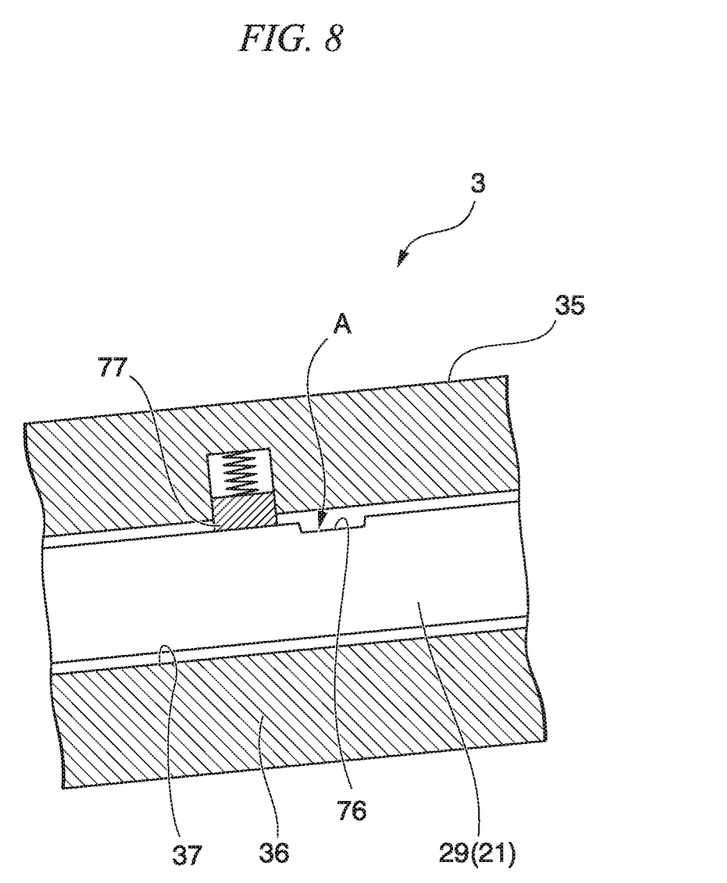
FIG. 8 is schematic cross-sectional view illustrating an endoscope in a medical system according to a fourth embodiment.

Next, a fourth embodiment of the invention will be described. FIG. 8 is a schematic cross-sectional view illustrating an endoscope in a medical system according to the fourth embodiment. As illustrated in FIG. 8, in the fourth embodiment, a recessed portion 76 provided at the sheath portion 29 of the treatment tool 21 serves as a first indicator portion, and a projecting portion 77 provided at the overtube 35 serves as a second indicator portion. That is, in a projecting and recessed structure including the recessed portion 76 and the projecting portion 77, a position where the recessed portion 76 and the projecting portion 77 are mated to each other is set to provide a positional relationship suitable for calibrating the treatment tool 21. In other words, while the projecting portion 77 is inserted into the recessed portion 76, the joint portion 22 of the treatment tool 21 is placed in a position where the calibration sensor 41 is arranged. The recessed portion 76 is provided with a switch that can be pressed by the projecting portion 77. The switch provided in the recessed portion 76 generates the detection signal 60 described in the first embodiment when the switch is pressed by the projecting portion 77. Alternatively, instead of the switch provided in the recessed portion 76, the detection signal 60 may be generated through a manual operation using an input means or the like (not shown) when an operator recognizes that the sheath portion 29 is fixed to the overtube 35 by the projecting portion 77 being inserted into the recessed portion 76.

Even in such a configuration, it is possible to calibrate the treatment tool 21 similar to the first embodiment. In addition, according to this embodiment, since a state in which the projecting portion 77 is inserted into the recessed portion 76 is a state in which the calibration can be performed, it is possible to detect a positional relationship using an easier and simpler configuration than that of the first embodiment.

(Modified Example)

Figure 9:
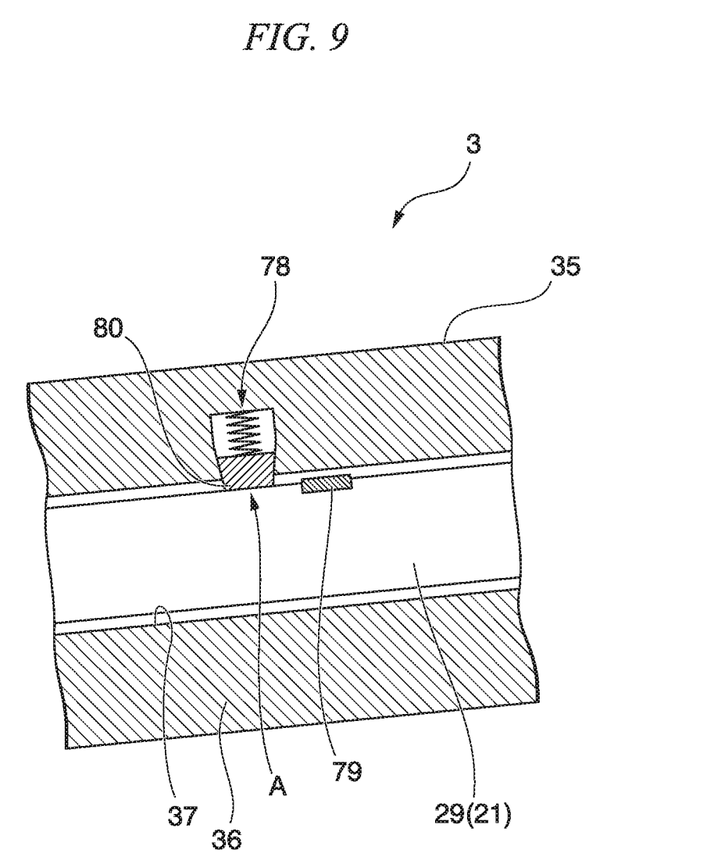
FIG. 9 is a schematic cross-sectional view illustrating a modified example of the fourth embodiment.

Instead of the projecting and recessed structure described in the embodiment, each of the first and second indicator portions may have an electrical contact in order to determine that the first and second indicator portions have a predetermined positional relationship when the first and second indicator portions come into contact. FIG. 9 is a schematic cross-sectional view illustrating a modified example of the endoscope in the medical system according to the fourth embodiment. In this modified example, as illustrated in FIG. 9, a contact target 79 electrically connected to the control unit 50 (refer to FIG. 3) is arranged as a first indicator portion at the sheath portion 29, and a contactor 80 electrically connected to the control unit 50 is arranged as a second indicator portion at the overtube 35, so that the contact target 79 and the contactor 80 constitute a set of contact sensors 78. In this modified example, it is detected that the first and second indicator portions have the predetermined positional relationship when the contact target 79 and the contactor 80 are electrically conductive with each other. Therefore, it is possible to calibrate the treatment tool 21 similar to the embodiments described above.

(Fifth Embodiment)

Figure 10:
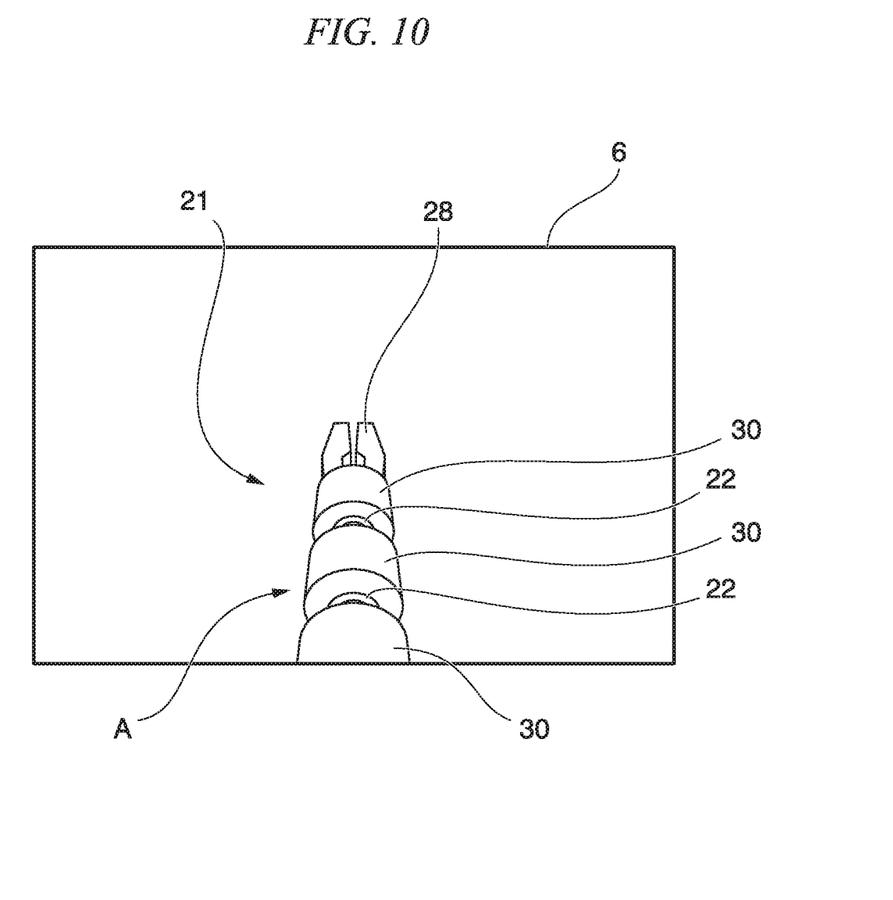
FIG. 10 illustrates an exemplary display screen of a display device in a medical system according to a fifth embodiment.

Next, a fifth embodiment of the invention will be described. FIG. 10 is a diagram illustrating an exemplary image displayed on a display device in a medical system according to this embodiment. In this embodiment, the imaging portion 39 (an imaging unit) illustrated in FIG. 2 can be used as a second indicator portion that detects the first indicator portion 24. In addition, although the first indicator portion 24 may have the same configuration as the first embodiment, the first indicator portion 24 may be a portion of the treatment tool 21 that has a shape by which a characteristic point can be extracted, such as the arm portion 30 or the joint portion 22 of the treatment tool 21. In this embodiment, calibration can be performed when the arm portion 30 or the joint portion 22 of the treatment tool 21 is placed within a field of view of the imaging portion 39 as illustrated in FIG. 10 in a state in which the arm portion 30 or the joint portion 22 of the treatment tool 21 is exposed from the distal end of the treatment tool channel 37. It should be noted that an image during calibration may not necessarily be displayed on the display device 6. When the image during calibration is displayed on the display device 6, an operator can visually recognize the calibration state. In this embodiment, a space A in which the calibration can be performed is defined by the field of view of the imaging portion 39. In addition, for example, if the cap 73 described in the second embodiment is attached to the overtube 35, the space A in which the calibration can be performed may be set inside the cap 73. The calibration of the treatment tool 21 in this embodiment can be executed based on image recognition for an image obtained by the imaging portion 39 and a measurement of a drive amount or a torque of the motor 27 in the treatment tool driving portion 26.

According to this embodiment, compared to the first embodiment, it is possible to provide a simpler and easier structure because the calibration sensor 41 is not necessary.

(Sixth Embodiment)

Figure 11:
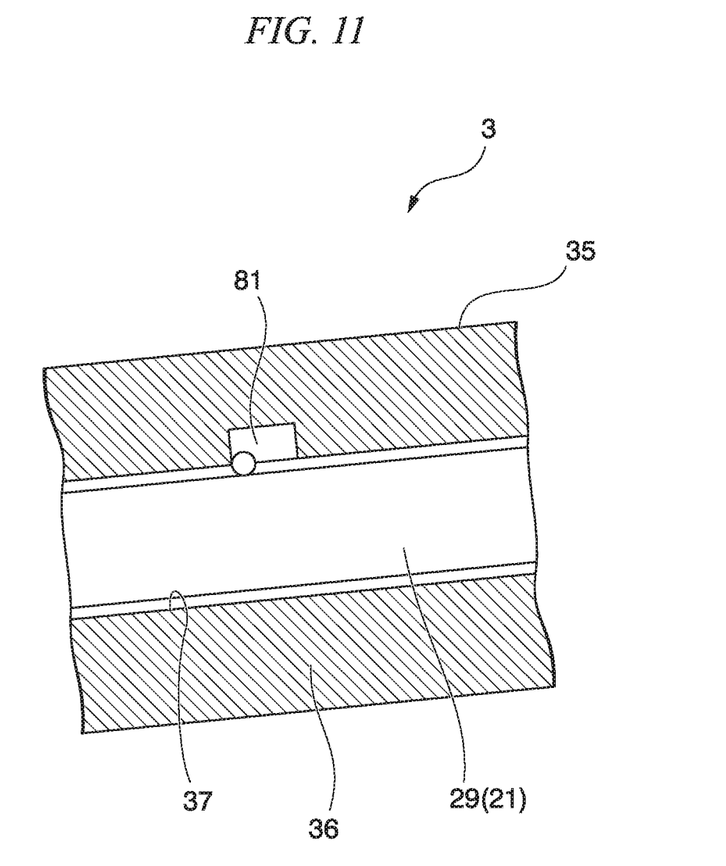
FIG. 11 is a schematic cross-sectional view illustrating an endoscope in a medical system according to a sixth embodiment.

Next, a sixth embodiment of the invention will be described. FIG. 11 is a cross-sectional view illustrating an endoscope in a medical system according to the sixth embodiment. As illustrated in FIG. 11, in the sixth embodiment, the sheath portion 29 of the treatment tool 21 serves as a first indicator portion, and an encoder 81 provided at the overtube 35 serves as a second indicator portion. That is, in this embodiment, the encoder 81 corresponds to the detecting means that detects a position of the sheath portion 29. The encoder 81 is electrically connected to the control unit 50 (refer to FIG. 3). The encoder 81 is arranged inside the treatment tool channel 37 such that the encoder 81 can come in contact with an outer circumferential surface of the sheath portion 29. The encoder 81 rotates when the sheath portion 29 advances or retracts inside the treatment tool channel 37 and comes in contact with the outer circumferential surface of the sheath portion 29. Furthermore, the encoder 81 outputs rotation number information for measuring a movement amount of the sheath portion 29.

The rotation number information of the encoder 81 is processed by the control unit 50 as the movement amount of the sheath portion 29. As a result, a position of the treatment tool 21 inside the treatment tool channel 37 can be detected by the control unit 50. Here, the control unit 50 estimates the position of the joint portion 22 based on the movement amount of the sheath portion 29, and enables starting of the calibration when the joint portion 22 is positioned at the calibration sensor 41 (for example, refer to FIG. 2). The estimation of the position of the joint portion 22 using the control unit 50 can be performed when the control unit 50 obtains configuration information on the treatment tool 21 and the treatment tool channel 37, such as positional information on the joint portion 22 with respect to the sheath portion 29 and information on the length of the treatment tool channel 37, in advance. In this embodiment, similar to the first embodiment, the calibration space A is set to the inside of the treatment tool channel 37 in the vicinity of the distal end of the treatment tool channel 37 (refer to FIG. 2).

According to this embodiment, it is possible to calibrate the treatment tool 21 similar to the first embodiment. In addition, according to this embodiment, since the rotation number information of the encoder 81 is referenced, it is possible to arrange each part of the joint portion 22, such as a hand side or a leading end side of the joint portion 22, in the calibration sensor 41. As a result, for example, it is possible to calibrate the hand side and the leading end side of the joint portion 22 in a different order.

While preferred embodiments of the invention and modified examples thereof have been described and illustrated hereinbefore, it should be understood that they are only for exemplary purposes and are not to be construed as limiting. Any addition, omission, substitution, or modification may be possible without departing from the spirit and scope of the present invention. Further, the elements described in each embodiment may be suitably combined. Accordingly, the invention is not to be considered as being limited by the foregoing description, and is only limited by the scope of the appended claims.

What is claimed is:

1. A medical system comprising:
    a treatment tool including: a treatment device configured to treat a living body; a joint configured to move the treatment device; a first indicating device provided to correspond to a position of the joint; a sheath connected to the joint; and a motor connected to the sheath, the motor configured to displace the joint;
    an overtube including: a flexible tube having a distal end and a proximal end, the flexible tube holding the treatment tool such that the treatment device is capable of protruding from the distal end; and a second indicating device provided at the flexible tube to identify a predefined space in which calibration of the treatment tool is performed; and
    a controller comprising hardware, the controller configured to calibrate the treatment tool when the first indicating device and the second indicating device have a predetermined positional relationship, wherein one of the first indicating device and the second indicating device is a magnet and the other of the first indicating device and the second indicating device is a magnetic detector.

2. The medical system according to claim 1, wherein the first indicating device is configured to determine that the first indicating device and the second indicating device have the predetermined positional relationship when the second indicating device is positioned closer than a predetermined distance.

3. The medical system according to claim 1, wherein the overtube includes a channel into which the treatment device, the joint, the first indicating device, and the sheath are capable of being inserted, and the space is defined inside the channel.

4. The medical system according to claim 1, wherein the controller is configured to start calibration only when the first indicating device and the second indicating device have the predetermined positional relationship.

5. The medical system according to claim 1, wherein the controller is further configured to:
    to detect a positional relationship between the first indicating device and the second indicating device and determine whether or not the first indicating device and the second indicating device have the predetermined positional relationship; and
    to start calibration when a state changes from a state in which the controller determines that the first indicating device and the second indicating device do not have the predetermined positional relationship to a state in which the controller determines that the first indicating device and the second indicating device have the predetermined positional relationship.

6. The medical system according to claim 1, wherein the controller is further configured to:
    detect a positional relationship between the first indicating device and the second indicating device and determine whether or not the first indicating device and the second indicating device have the predetermined positional relationship; and
    interrupt or terminate calibration when the calibration is being executed and a state changes from a state in which the controller determines that the first indicating device and the second indicating device have the predetermined positional relationship to a state in which the controller determines that the first indicating device and the second indicating device do not have the predetermined positional relationship.

7. A medical system comprising:
    a treatment tool including: a treatment device configured to treat a living body; a joint configured to move the treatment device; a first indicating device provided to correspond to a position of the joint; a sheath connected to the joint; and a motor connected to the sheath, the motor configured to displace the joint;
    an overtube including: a flexible tube having a distal end and a proximal end, the flexible tube holding the treatment tool such that the treatment device is capable of protruding from the distal end; and a second indicating device provided at the flexible tube to identify a predefined space in which calibration of the treatment tool is performed; and
    a controller comprising hardware, the controller configured to calibrate the treatment tool when the first indicating device and the second indicating device have a predetermined positional relationship, wherein the first indicating device comprises a sensor configured to image the first indicating device.

8. A medical system comprising:
    a treatment tool including: a treatment device configured to treat a living body; a joint configured to move the treatment device; a first indicating device provided to correspond to a position of the joint; a sheath connected to the joint; and a motor connected to the sheath, the motor configured to displace the joint;
    an overtube including: a flexible tube having a distal end and a proximal end, the flexible tube holding the treatment tool such that the treatment device is capable of protruding from the distal end; and a second indicating device provided at the flexible tube to identify a predefined space in which calibration of the treatment tool is performed; and
    a controller comprising hardware, the controller configured to calibrate the treatment tool when the first indicating device and the second indicating device have a predetermined positional relationship, wherein the first indicating device and the second indicating device include a projecting and recessed structure in which the first indicating device and the second indicating device are mated to each other when the first indicating device and the second indicating device have the predetermined positional relationship.

\* \* \* \* \*